United States Patent [19]
Petito

[11] Patent Number: 5,929,050
[45] Date of Patent: Jul. 27, 1999

[54] CHONDROITIN SULFATE COMPOSITION AND METHOD FOR WOUND TREATMENT

[76] Inventor: George D. Petito, 1890 Bucknell Dr., Bethlehem, Pa. 18015

[21] Appl. No.: 09/031,831

[22] Filed: Feb. 27, 1998

[51] Int. Cl.⁶ .................................................. A61K 31/715
[52] U.S. Cl. .................................................. 514/54; 514/2
[58] Field of Search ............................................ 514/54, 2

[56] References Cited

U.S. PATENT DOCUMENTS

| | | | |
|---|---|---|---|
| 4,006,224 | 2/1977 | Prudden | 424/180 |
| 4,640,912 | 2/1987 | Hausman | 514/54 |
| 4,808,570 | 2/1989 | Michaeli | 514/2 |
| 4,837,024 | 6/1989 | Michaeli | 424/446 |
| 4,863,907 | 9/1989 | Sakurai et al. | 514/56 |
| 4,983,580 | 1/1991 | Gibson | 514/2 |
| 5,366,964 | 11/1994 | Lindstrom et al. | 514/57 |
| 5,399,351 | 3/1995 | Leshchiner et al. | 424/422 |
| 5,498,606 | 3/1996 | Soll et al. | 514/54 |

*Primary Examiner*—Kathleen K. Fonda
*Attorney, Agent, or Firm*—Richard C. Litman

[57] ABSTRACT

A method and composition for treating open wounds. The method includes thorough cleaning of the wound, and application of the composition and a sterile dressing. The composition and dressing may be changed as needed. The composition is an aqueous solution of 90–110 mg/mL glycosaminoglycan. Preferably, chondroitin sulfate will be used. Additional components, that may be added singly or in combination, include collagen, other glycosaminoglycans, glucosamine hydrochloride, glucosamine sulfate, certain buffering agents, and certain preservatives. Using the solution of this invention on acute or chronic open wounds aids the natural healing process, thereby increases the rate of healing.

9 Claims, No Drawings

CHONDROITIN SULFATE COMPOSITION AND METHOD FOR WOUND TREATMENT

BACKGROUND OF THE INVENTION

1. Field of the Invention

The present invention relates to compositions and methods that increase the rate at which a wound will heal.

2. Description of Related Art

Glycosaminoglycans (GAGs) are polysaccharides found in vertebrate and invertebrate animals. Several GAGs have been found in tissues and fluids of vertebrate animals. The known GAGS are chondroitin sulfate, keratan sulfate, dermatan sulfate, hyaluronic acid, heparin and heparan sulfate.

Chondroitin sulfate is a linear polymer occurring in several isomers, named for location of the sulfate group. Chondroitin-4 sulfate is found in nasal and tracheal cartilages of bovines and porcines. It is also found in the bones, flesh, blood, skin, umbilical cord, and urine of these animals. Chondroitin-6 sulfate has been isolated from the skin, umbilical cord, and cardiac valves of these animals. Chondroitin-6 sulfate has the same composition, but slightly different physical properties from chondroitin-4 sulfate. These are the most common isomers used in the present invention. The polymer is also known as chondroitin polysulfate sodium, chondron, sodium chondroitin poly sulfate, and sodium chondroitin sulfate. For consistency, the term "chondroitin sulfate" will be used for all chondroitin sulfate isomers throughout this application. Chondroitin sulfate is involved in the binding of collagen and is also directly involved in the retention of moisture. These are both properties that aid the healing process.

Open wounds on the skin are a potential gateway for infection to enter the body. The skin is an exterior protective barrier to outside contaminants. When the skin is damaged, with an open breach, these contaminants are free to enter the body. Once inside the body, these contaminants may have effects of varying degree, but almost always become more difficult to treat and slow the healing process of the original wound.

Just as nature has provided the skin as a barrier for protection, it has also provided mechanisms for repair of the skin. Depending upon the nature of the injury, this repair process may take hours, days, months, or even years. Many factors determine the length of time it takes to heal. That pathogenic contaminants may enter the body through the wound until the skin's integrity is restored, however, is certain. For this reason, it is desirable to heal open wounds as quickly as possible.

To fight infection, wound management traditionally involves an initial cleansing of the affected area to remove any contaminants such as dirt, clothing particles, or other debris. Damaged materials or tissues are removed when necessary, and antiseptic agents applied to sterilize the area. Sterile dressings are often applied, and periodically changed, to keep the area as clean and sterile as possible. Complex biological mechanisms occur during the healing process. During the process, chemical signals call fibroblasts to the wound site, ultimately generating connective structures mainly of collagen. Endothelial cells generate new blood capillaries that feed the new growth. The cell growth continues until the wound is filled, forming permanent new tissue.

Because shortened periods of healing mean shortened exposure time, it would be beneficial to have open wounds heal as quickly as possible. Likewise, it would be beneficial if a medical practitioner could apply a product, using the healing advantages of chondroitin sulfate and other GAGs, to an open wound to speed the healing process.

Chondroitin sulfate, and other GAGs, used to aid healing or trauma have been the subject of previous patents. U.S. Pat. No. 4,808,570, which issued to Michaeli on Feb. 28, 1989, discloses compositions and method for improving wound healing that uses GAGs, but teaches against the use of chondroitin sulfate. U.S. Pat. No. 4,640,912, issued to Hausman on Feb. 3, 1987, discloses the use of "active" chondroitin sulfate A and "active" chondroitin sulfate C to prevent cancer cell implantation, bacterial infestation, trauma, irritation or damage from foreign instruments in the kidney, renal pelvis, ureter, bladder, urethra, etc. by irrigation with a solution containing the chondroitin sulfate.

U.S. Pat. No. 4,863,907, which issued to Sakurai, et al. on Sep. 5, 1989, discloses cross-linked glycosaminoglycans and their use. The patent discloses cross-linked glycosaminoglycans, with a cross-linking index of 0.05 or more per mole, for various medical and cosmetic uses.

U.S. Pat. No. 5,366,964, which issued to Lindstrom, et al. on Nov. 22, 1994, discloses a viscoelastic solution. The solution contains 0.01–10% chondroitin sulfate and 0.01–10% sodium hyaluronate among other ingredients for use in ocular and surgical applications.

U.S. Pat. No. 4,983,580, which issued to Gibson on Jan. 8, 1991, discloses methods and materials for use in corneal wound healing. A preferred embodiment includes fibronectin and chondroitin sulfate in a corneal mortar composition.

U.S. Pat. No. 5,498,606, which issued to Soll et al. on Mar. 12, 1996, discloses a method of protecting human and animal cells. According to the patent, an intra-articular injection of a compound containing 40–55% by weight chondroitin sulfate is used in protecting cells.

U.S. Pat. No. 5,399,351, which issued to Leshchiner, et. al. on Mar. 21, 1995, discloses the preparation and use of biocompatible viscoelastic gel slurries. According to this invention, a gel containing cross-linked glycosaminoglycans for controlling adhesion formation between tissues resulting from surgical intervention.

None of the above inventions and patents, taken either singularly or in combination, is seen to describe the instant invention as claimed. Thus a wound treatment using chondroitin sulfate solving the aforementioned problems is desired.

SUMMARY OF THE INVENTION

The present invention is a method and composition for treating open wounds. The composition is an aqueous solution of 90–110 mg/mL glycosaminoglycan. Preferably, chondroitin sulfate is used. Additional components, that may be added singly or in combination, include collagen, other glycosaminoglycans, glucosamine hydrochloride, glucosamine sulfate, certain buffering agents, and certain preservatives. Using the solution of this invention on acute or chronic open wounds aids the natural healing process. The healing process is "jump started" by attracting endothelial cells to the wound site, or chemotaxis. Epithelial cell growth and migration are also promoted by use of the solution. Cellular adhesion is also enhanced. Furthermore, the solution forms a protective tissue coating particularly useful after chronic wounds have been debrided. Use of the solution also inhibits bacterial infection. Accordingly, it is a principal object of the invention to speed the healing of open wounds.

It is another object of the invention to protect the wound from bacterial infestation.

It is a further object of the invention to increase chemotactic activity.

Still another object of the invention is to enhance the body's natural healing ability by making resources readily available.

It is an object of the invention to provide an improved product for the purposes described which is inexpensive, dependable and fully effective in accomplishing its intended purposes.

These and other objects of the present invention will become readily apparent upon further review of the following specification.

DETAILED DESCRIPTION OF THE PREFERRED EMBODIMENTS

The present invention is a method and composition used in aiding the healing of open wounds. Acute and chronic wounds are served equally well by the present invention. The composition is an aqueous solution of a glycosaminoglycan (GAG), alone or in combination with collagen, other GAGS, and glucosamine hydrochloride or glucosamine sulfate. The solution may also be used as a flushing or irrigation aid.

The base solution used is an aqueous solution of 90–110 g/mL GAG. The preferred GAG is chondroitin sulfate cultivated from a bovine source. Any of the isotopes for chondroitin sulfate, or combination thereof, may be used when making the solution. Preferably chondroitin sulfate having a molecular weight range between 5,000 and 50,000 will be used. Most preferably, this range will be limited to 25,000 to 35,000. The presence of the GAG at the wound site increases chemotactic activity, attracting endothelial cells. The increased attraction and presence of endothelial cells speeds the healing process.

To increase the efficacy of the solution, and further catalyze the healing process, collagen is added to the solution. Collagen is a fibrous protein material that is found in the skin, bones, tendons, cartilage, blood vessels, and teeth of mammals. Collagen serves to hold various body structures together, and takes on a directive role during the healing process. The addition of collagen to the solution immediately provides building materials for the body to use during the normal course of healing.

Additionally, sodium hyaluronate and glucosamine hydrochloride or glucosamine sulfate may be combined with the solution. The addition of these compounds reduces inflammation at and around the wound site. Reduction and prevention of inflammation allows vital energy to be directed toward healing the wound. Furthermore, where hydrolyzed collagen is used, synergy and chemical bonding for cell surface interaction are enhanced.

Buffers and preservatives may also be added to increase the useful shelf-life of the solution. Potential buffering agents include citric acid, monosodium phosphate, dibasic-sodium phosphate, sodium chloride, etc. Possible preservative that may be used include ethylenediaminetetraacetic acid (EDTA), benzyl alcohol, benzalkonium chloride, etc. The solution is equally effective with or without these buffers and preservatives.

Regardless of the specific formulation of the solution as noted, application of the solution is as follows The wound must first be cleansed thoroughly and decontaminated per standard medical practice. A clean and sterile wound surface is desired. A quantity of the present solution is applied to all surfaces of the wound site. A sterile gauze, or similar, dressing may then be placed over the wound. On a periodic basis, the dressing should be removed and the wound cleaned according to standard medical practices. The solution may then be reapplied, and sterile dressing replaced. Application of the solution continues until the wound has completely healed. The solution may also be injected into traumatized areas such as joints, muscles, or other tissues with similar healing effects.

It is to be understood that the present invention is not limited to the embodiments described above, but encompasses any and all embodiments within the scope of the following claims

I claim:

1. A method for treating open wounds comprising the step of applying to a wound an effective amount of an aqueous solution comprising 90–110 mg/mL chondroitin sulfate.

2. The method for treating open wounds defined in claim 1 wherein said aqueous solution further comprises collagen.

3. The method for treating open wounds defined in claim 1 wherein said aqueous solution further comprises sodium hyaluronate, glucosamine hydrochloride, and hydrolyzed collagen for aiding anti-inflammatory response.

4. The method for treating open wounds defined in claim 1 wherein said aqueous solution further comprises sodium hyaluronate, glucosamine sulfate, and hydrolyzed collagen for aiding anti-inflammatory response.

5. A method for treating traumatized areas comprising the step of injecting into the area an effective amount of an aqueous solution consisting of 90–110 mg/mL chondroitin sulfate.

6. An aqueous solution for treating open wounds comprising 90–110 mg/mL chondroitin sulfate.

7. The aqueous solution as defined in claim 6 further comprising collagen.

8. The aqueous solution as defined in claim 6 further comprising sodium hyaluronate, glucosamine hydrochloride, and hydrolyzed collagen for aiding anti-inflammatory response.

9. The aqueous solution as defined in claim 6 further comprising sodium hyaluronate, glucosamine sulfate, and hydrolyzed collagen for aiding anti-inflammatory response.

* * * * *